US008440615B2

(12) United States Patent
Dal Farra et al.

(10) Patent No.: US 8,440,615 B2
(45) Date of Patent: May 14, 2013

(54) PHARMACEUTICAL AND/OR COSMETIC COMPOSITION CONTAINING ACTIVE-PRINCIPLE ACTIVATORS OF ACONITASE (75) Inventors: Claude Dal Farra, Opio (FR); Nouha Domloge, Valbonne (FR); Jean-Marie Botto, Valonne (FR)

(73) Assignee: Societe d'Extraction des Principes Actifs (Vincience), Biot (FR)

( * ) Notice: Subject to any disclaimer, the term of this patent is extended or adjusted under 35 U.S.C. 154(b) by 685 days.

(21) Appl. No.: 12/597,873

(22) PCT Filed: Apr. 23, 2008

(86) PCT No.: PCT/FR2008/000572
§ 371 (c)(1),
(2), (4) Date: Oct. 27, 2009

(87) PCT Pub. No.: WO2008/145849
PCT Pub. Date: Dec. 4, 2008

(65) Prior Publication Data
US 2010/0286037 A1 Nov. 11, 2010

(30) Foreign Application Priority Data

Apr. 27, 2007 (FR) .................................. 07 03053

(51) Int. Cl.
*A61K 38/07* (2006.01)
*A61K 38/08* (2006.01)
*A61K 38/06* (2006.01)
*A61P 17/00* (2006.01)
*A61P 3/10* (2006.01)
*A61P 9/00* (2006.01)
*A61P 25/00* (2006.01)

(52) U.S. Cl.
USPC ......... 514/6.9; 514/16.4; 514/17.7; 514/18.8; 514/21.8; 514/21.9

(58) Field of Classification Search .................. None
See application file for complete search history.

(56) References Cited

U.S. PATENT DOCUMENTS 5,728,680 A * 3/1998 Morozov et al. ............. 514/13.5
6,562,786 B1 * 5/2003 Blaschuk et al. ............ 514/19.1
(Continued)

FOREIGN PATENT DOCUMENTS

| WO | 98/36748 | 8/1998 |
|---|---|---|
| WO | 02/064129 | 8/2002 |
| WO | 2004/043482 | 5/2004 |

OTHER PUBLICATIONS

Rzymkiewicz D. et al., "Induction of heme oxygenase-1 modulates cis-aconitase activity in lens epitelial cells" Biochem Biophys Res Comm, vol. 270, Apr. 2, 2000, XP002461446, pp. 324-328, (abstract only).

(Continued)

*Primary Examiner* — Robert A Wax
*Assistant Examiner* — William Craigo
(74) *Attorney, Agent, or Firm* — Young & Thompson (57) ABSTRACT

A cosmetic or pharmaceutical composition, and in particular a dermatological one, including, in a physiologically adapted medium, active principles capable of activating aconitase, and methods of using the composition for protection of mitochondria, the skin and the appendages from external aggressions and to combat cutaneous aging. These active principles may be composed of polypeptides or of peptides, used alone or in association with at least one other active principle.

18 Claims, 1 Drawing Sheet

U.S. PATENT DOCUMENTS

| | | |
|---|---|---|
| 7,504,092 B2 | 3/2009 | Dal Farra et al. |
| 2003/0152578 A1* | 8/2003 | Ruoslahti et al. .......... 424/178.1 |
| 2004/0033538 A1 | 2/2004 | Masuda et al. |
| 2004/0086526 A1 | 5/2004 | Danoux et al. |
| 2005/0079186 A1* | 4/2005 | Papierok et al. ........... 424/185.1 |
| 2006/0257411 A1* | 11/2006 | Beutler et al. ............. 424/159.1 |

OTHER PUBLICATIONS

International Search Report dated May 7, 2009, from corresponding PCT application.

* cited by examiner

PHARMACEUTICAL AND/OR COSMETIC COMPOSITION CONTAINING ACTIVE-PRINCIPLE ACTIVATORS OF ACONITASE

The present invention is in the cosmetic and pharmaceutical domain, and more particularly in the domain of dermatology. The present invention concerns a cosmetic or pharmaceutical composition, and particularly a dermatological one, comprising, in a physiologically adapted medium, active principles capable of activating aconitase. These active principles may be polypeptides or peptides, used alone or in association with at least one other active principle. The invention is also related to the use of a composition capable of protecting mitochondria. The invention also concerns a cosmetic-treatment procedure intended to protect the skin and the appendages from external aggressions and to combat cutaneous aging. The said peptides, protectors of mitochondria, can also be used to prepare pharmaceutical compositions intended to prevent or combat pathologies linked to mitochondrial dysfunctions, for example, certain neuromuscular or cardiac degenerations, type II diabetes, or even certain pathologies of aging.

The term "appendages" according to the invention encompasses the assemblage of keratinic appendices exhibited on the body surface, in particular the hair, eyelashes, eyebrows, nails, and hair.

The mitochondria are organelles of eucaryote cells specialized in energy production. They are endowed with their own DNA (DNAmt). The energy produced by the respiratory chain is stored in the form of ATP. Under certain conditions of cellular stress, the electrons, released by the respiratory chain by oxidative phosphorylation produce free radicals that can damage the mitochondrial structures. These stress factors may be intrinsic or of external origin. Among the latter, UV rays, toxins, radiation, and alimentary oxidants may be cited. Thus, a progressive decline in mitochondrial functions with age can also be shown, probably linked to the accumulation of mutations on DNAmt (K. Singh (2004), *Ann. NY Acad. Sci.*, 1019). These DNAmt mutations can be induced by repeated exposure to UV rays and will even be evidence of photo-aging (W. Berneburg et al. (2004), *J. Invest. Dermatol.* 122(5).

The mitochondria also play a central role in apoptosis. Mitochondrial degradation may thus be a factor initiating the series of reactions leading to apoptosis in numerous cell types (G. Kroemer et al. (1995), *FASEB J.* 9: 1277-87.

Natural repair mechanisms have been identified in the mitochondria. Aconitase (aconitase hydratase or iron regulatory protein; EC 4.2.1.3) has thus been discovered to be indispensible for the maintenance of DNAmt integrity, independent of its catalytic activity. Aconitase was first of all identified as a mitochondrial enzyme implicated in the Krebs cycle; it catalyzes the stereospecific conversion of citrate to isocitrate and thus participates in the energy production of the cell. It possesses an active site including an iron-sulfur aggregate (4Fe-4S) with a pseudocubic geometry. Recently, the team of Dr. Butow (X. J. Chen et al. (2005), *Science* 307) was able to show that aconitase plays a key role in preserving the integrity of mitochondrial DNA. It interacts with the DNA within regulatory regions, suggesting a role in the packing of the mitochondrial genome in the manner of a protein in the HSP 70 family. The transition from the form connecting the DNA to the active form of the enzyme will be based on the assembling or disassembling of the iron-sulfur cluster.

Thanks to its double functionality, aconitase establishes a direct link between the energy-generating activity of the mitochondrion and the preservation of DNAmt. Aconitase could thus constitute a therapeutic target for preventing or combating pathologies linked to mitochondrial dysfunctions, for example, type II diabetes, certain neuromuscular conditions, or certain pathologies of aging.

The search for compounds capable of stimulating or protecting the mitochondria is an important concern of medical research and of cosmetics. Concerning the skin, these new compounds could be useful in preventing or combating the signs of cutaneous aging, as well as in protecting or repairing the skin after burns, exposure to UV rays or radiation, or exposure to toxins or to pollutants.

In order to protect the mitochondria and to combat the associated pathologies or the effects of cutaneous aging, solutions have been proposed such as intake of substances implicated in energy metabolism, and more particularly, intermediaries or cofactors of the Krebs cycle such as fumarate, L-malate, acetyl CoA (WO 02064129), or even treating the skin with substances capable of reducing free radicals, such as vitamin C (US 2004/0086526) or L-ergothionine (WO 9836748). But, to the knowledge of the applicant, a composition containing active principles capable of activating aconitase and its use, with the aim of protecting the mitochondria and of combating the associated pathologies and/or the effects of cutaneous aging, has never been described.

The present invention has a principal objective of providing a new active principle capable of protecting the skin from external aggressions and of combating cutaneous aging. The inventors have in effect highlighted a therapeutic activity, and more particularly a dermatological and cosmetic one, of peptides capable of activating aconitase. It has been particularly brought out that these peptides, when they are applied on the skin, promote mitochondrial activity in a significant way, demonstrated by an increased activity of the enzyme aconitase and an increase in the synthesis of ATP. These new active principles, protectors of the mitochondria, thus open up new therapeutic and cosmetic perspectives.

Thus, the invention has as its first object a cosmetic or pharmaceutical composition, characterized by the fact that it contains, as an active-principle protector of the mitochondria, in a physiologically adapted medium, alone or in association with at least one other active principle, a peptide capable of activating aconitase.

An "active-principle protector of mitochondria or capable of protecting mitochondria" is understood to be any substance capable of limiting the functional or structural alterations of cell or tissue mitochondria subjected to a physicochemical or environmental stress.

A "peptide capable of activating aconitase" is understood to be any peptide or polypeptide capable of increasing aconitase, cytoplasmic and/or mitochondrial, either by activating the proteinic synthesis of aconitase (by means of direct or indirect modulation of the gene expression of the aconitase), or by increasing the enzymatic activity of aconitase, or by other biological processes such as the stabilization of the aconitase protein or even the stabilization of the messenger RNA transcripts.

The term "peptide" designates a chaining of two or several amino acids linked to one another by peptide bonds or by modified peptide bonds, the term "polypeptide" designating a peptide of greater size.

"Peptide" must be understood to be the natural or synthetic peptide of the invention as described above or at least one of its fragments, which is either obtained by proteolysis or synthetically, or even any natural or synthetic peptide whose sequence is wholly or partially composed of the sequence of the peptide according to the invention.

Preferentially, according to the present invention, the active-principles activators of aconitase or their biologically active derivatives are peptides in which the number of amino acids is between 3 and 14.

The expression "biologically active" is understood as "that possesses an in vivo or in vitro activity characteristic of the activity of the active principle according to the invention".

According to a particularly advantageous embodiment of the invention, the peptide possesses a sequence that answers to the general formula (I)

$$R_1\text{-}(AA)_n\text{-}X_1\text{-}X_2\text{-}X_3\text{-}X_4\text{-}X_5\text{-}X_6\text{-}(AA)_p\text{-}R_2$$

where
- $X_1$ is serine,
- $X_2$ is cysteine,
- $X_3$ is threonine or isoleucine,
- $X_4$ is glutamine or aspargine, or no amino acid,
- $X_5$ is threonine, serine, or no amino acid,
- $X_6$ is isoleucine, glutamine, or no amino acid.
- AA represents any amino acid whatever, or one of its derivatives, lacking the sequence of aconitase, and n and p are whole numbers between 0 and 4.
- $R_1$ represents the primary amine function of the N-terminal amino acid, free or substituted with a protector group which may be chosen from an acetyl group, a benzoyl group, a tosyl group, or a benzyloxycarbonyl group.
- $R_2$ represents the hydroxyl group of the carboxylic acid function of the C-terminal amino acid, free or substituted with a protector group which can be chosen from an alkyl chain of $C_1$ to $C_{20}$, or an $NH_2$, NHY, or NYY group, with Y representing a alkyl chain of $C_1$ to $C_4$.

According to one, most especially preferred embodiment of the invention, the biologically active peptide has the sequence:

```
(SEQ ID No. 1)    Ser-Cys-Ile-Asn-Thr (SEQ ID No. 2)    Ser-Cys-Ile-Asn-Thr-NH2

(SEQ ID No. 3)    Ser-Cys-Thr-Asn-Thr (SEQ ID No. 4)    Ser-Cys-Thr-Asn-Thr-NH2

(SEQ ID No. 5)    Ser-Cys-Ile-Asn-Ser (SEQ ID No. 6)    Ser-Cys-Ile-Gln (SEQ ID No. 7)    Ser-Cys-Thr
```

According to one particularly interesting embodiment, the biologically active peptide corresponds to the sequence SEQ ID No. 1.

According to another particularly interesting embodiment, the biologically active peptide corresponds to the sequence SEQ ID No. 2.

The invention also concerns homologous forms of these sequences. The term "homologous" designates, according to the invention, any peptide sequence identical to at least 50%, or preferably to at least 80%, and even more preferentially to at least 90%, of said peptide sequence, chosen from among the sequences SEQ ID No. 1 to SEQ ID No. 7. A "peptide sequence identical to at least X %" is understood to designate a identity percentage between the residues of amino acids of the two sequences to be compared, obtained after the optimal alignment of the two sequences. The optimal alignment is obtained using algorithms for local homologies such as those used by the BLAST P or T BLAST N computer software available on the National Center for Biotechnology Information (NCBI) website.

The term "homologous" can also designate a peptide that differs from the sequence of a peptide with sequence SEQ ID No. 1 to SEQ ID No. 7 by the substitution of chemically equivalent amino acids, that is, by the substitution of one residue by another possessing the same characteristics. Thus, the classic substitutions are made between Ala, Val, Leu, and Ile; between Ser and Thr; between the acid residues of Asp and Glu; between Asn and Gln; and between the basic residues of Lys and Arg or between the aromatic residues of Phe and Tyr.

In the invention, the term "amino acid" refers here to any natural or synthetic organic acid having the formula:

—NHR—CR—C(O)—O— where each —R is independently selected from a hydrogen or an alkyl group having between 1 and 12 carbon atoms. Preferentially, at least one —R group of each amino acid is a hydrogen. The term "alkyl" is understood here to be a carbon chain which can be linear or branched, substituted (mono- or poly-) or unsubstituted; saturated, mono-saturated (a double or triple bond in the chain) or polyunsaturated (two or several double bonds, two or several triple bonds, one or several double bonds and one or several triple bonds in the chain).

So as to improve resistance to degradation, it may be necessary to utilize a protected form of the peptide according to the invention. The form of protection shall of course be a biologically compatible form and shall be compatible with a use in the domain of cosmetics or of pharmaceuticals.

Numerous biologically compatible forms of protection may be envisioned. These are well-known to the professional, such as, for example, the acylation or acetylation of the amino-terminal end, or the amidation or esterification of the carboxy-terminal end. Thus, the invention concerns a composition as previously defined, characterized by the fact that the peptide with sequence SEQ ID No. 1 to SEQ ID No. 7 is in a protected form or not. A protection may be used which is based on a substitution on the amino-terminal end by an acetyl group, a benzoyl group, a tosyl group, or a benzyloxycarbonyl group. Preferably, a protection is used which is based on the amidation of the hydroxyl function of the carboxy-terminal end by an NYY group, with Y representing an alkyl chain of $C_1$ to $C_4$, or esterification by an alkyl group. It is also possible to protect both the ends of the peptide.

The peptide derivatives also concern amino acids and peptides connected to one another by a pseudo-peptide bond. A "pseudo-peptide bond" is understood to be all the types of bond likely to replace the "classic" peptide bonds.

In the domain of the amino acids, the geometry of the molecules is such that they can theoretically exhibit the form of different optical isomers. Indeed, there exists one molecular conformation of the amino acid (AA) such that it deflects the plane of light polarization to the right (dextrorotatory or D-aa conformation), and a molecular conformation of the amino acid (aa) such that it deflects the plane of light polarization to the left (levorotatory or L-aa conformation). The nature of the natural amino acids is such that it retains only the levorotatory conformation. Consequently, a peptide of natural origin will be composed only of amino acids of the L-aa type. However, chemical synthesis in the laboratory enables amino acids to be prepared which have both possible conformations. Starting with this material as a base, it is thus possible, during peptide synthesis, to incorporate equally well amino acids in the form of dextrorotatory or levorotatory optical isomers. Thus, the amino acids composing the peptide according to the invention may be in the L or D configuration; preferentially, the amino acids are in the L form. The peptide according to the invention can thus be in an L, D, or DL form.

The peptide with general formula (I) according to the invention can be obtained either by classical chemical synthesis (in solid phase or homogeneous liquid phase) or by enzymatic synthesis (Kullman et al. (1980), *J. Biol. Chem.*, 225, 8234), starting from the constituent amino acids or from their derivatives.

The peptide according to the invention can also be obtained by fermentation of a strain of bacteria, modified or not by genetic engineering, or even by extraction of proteins of animal or vegetable origin, preferentially of vegetable origin, followed by a controlled hydrolysis which releases peptide fragments which correspond in whole or in part to the peptides with general formula (I).

A great many proteins found in plants are likely to contain these sequences within their structure. Controlled hydrolysis enables these peptide fragments to be released. It is possible, but not necessary to achieve the invention, either to extract the proteins concerned first and then to hydrolyze them, or to perform the hydrolysis first on a raw extract and to subsequently purify the peptide fragments. It is also possible to use certain hydrolyzed extracts without purifying the peptide fragments in them which correspond to peptides with the general formula (I) according to the invention, but at the same time ensuring the presence of the said fragments by appropriate analytical means.

Other procedures, simpler or more complex, may be envisioned by the professional familiar with the craft of synthesis, extraction, and purification of proteins and peptides. Thus, the peptide according to the invention can be of natural or synthetic origin. Preferentially according to the invention, the peptide is obtained by chemical synthesis.

According to the invention, the active principle can be a mixture of peptide derivatives and/or constituents of amino acid derivatives.

According to one advantageous embodiment of the invention, the polypeptides or peptides with general formula (I) are solubilized in advance in one or several cosmetically or dermatologically acceptable solvents traditionally used by the professional, such as water, glycerol, ethanol, propylene glycol, butylene glycol, dipropylene glycol, ethoxylated or propoxylated diglycols, cyclic polyols, vaseline, a vegetable oil, or any mixture of these solvents.

According to yet another advantageous embodiment of the invention, the peptides possessing general formula (I) according to the invention are solubilized in advance in a cosmetic or pharmaceutical vehicle like the liposomes or adsorbed onto powdered organic polymers or mineral supports like the talcs and bentonites, and are more generally solubilized in, or fixed upon, any cosmetically or pharmaceutically acceptable vehicle.

It is of course understood that the peptide according to the invention can be used alone or in association with at least one other active principle, in a cosmetic composition or for the preparation of a pharmaceutical and/or dermatological composition.

The compositions according to the invention could be applied in any appropriate way, particularly oral, parenteral, or externally topical, and their formulation will be adapted by the professional, in particular for cosmetic or dermatological compositions. Advantageously, the compositions according to the invention are intended for administration by topical, cutaneous means. These compositions shall therefore contain a cosmetically and/or dermatologically acceptable medium, that is, compatible with the skin and the appendages, and they cover all the cosmetic or dermatological forms. These compositions could, in particular, be in the form of creams, oil-in-water or water-in-oil emulsions, or multiple emulsions, solutions, suspensions, gels, milks, lotions, sticks, or even powders, adapted to application onto the skin, the lips, and/or the appendages.

Of course, the professional will take care to choose possible supplementary compounds, active or not, and/or their quantity such that the advantageous properties of the mixture are not, or are not appreciably, altered by the addition envisaged.

These compositions include the excipients necessary for their formulation, such as solvents, thickeners, diluents, surfactants, antioxidants, colorants, preservatives, or perfumes.

The composition usable according to the invention can, in particular, consist of a composition for hair care, and particularly a shampoo, a conditioner, a blow-dry lotion, a treatment lotion, a cream or a styling gel, a restructuring lotion for the hair, a mask, etc. The cosmetic composition according to the invention can be used particularly in treatments implementing an application that is followed or not by a rinse, or even in the form of shampoo.

It can also come in the form of a dye or a mascara to be applied with brush or comb, in particular on the eyelashes, eyebrows, or hair.

Advantageously, the compositions usable according to the invention contain, in addition, other active principles promoting the action of the active principle according to the invention. For example, active principles may be added which have an anti-radical or antioxidant action, chosen from vitamin C, vitamin E, or coeznzyme Q10 or the polyphenolic extracts of plants.

"Active anti-radical principles" are understood to be any compound capable of trapping free radicals. These active principles are capable of blocking the chain reactions of free radicals before the final stages of degradation of the biological constituents of the skin, and because of this they have an antioxidant activity.

The composition according to the invention may also associate with the peptide activators of aconitase active principles stimulating the syntheses of dermal macromolecules (laminin, fibronectin, collagen), for example the collagen peptide marketed under the name of Collaxyl® by the Vincience Company.

The composition according to the invention may also associate with the peptide activators of aconitase active principles stimulating energy metabolism, like the active principle marketed under the name of GP4G® by the Vincience Company.

From another angle, the composition according to the invention may be a sun-related composition, that is, a composition that aids in protection against solar radiation. Thus, there may be advantageously added to the composition according to the invention active agents which aid in solar protection such as, for example, solar filters.

It is quite obvious that the invention is directed toward mammals in general and more particularly toward human beings.

The effective amount of active principle corresponds to the quantity necessary to obtain the result being sought, that is to say, to activate aconitase, protect the mitochondria, and thus protect the skin from external aggressions and combat cutaneous aging.

According to an advantageous embodiment of the invention, the peptide with general formula (I) is present in the compositions of the invention in a concentration between approximately 0.0005 and 500 ppm (parts per million), and preferentially in a concentration between approximately 0.01 and 5 ppm, relative to the total weight of the final composition.

These compositions could come particularly in the form of an aqueous, hydroalcoholic, or oily solution, an oil-in-water or water-in-oil emulsion, or multiple emulsions. They can also come in the form of creams, suspensions, or even powders, adapted to application onto the skin, the mucous membranes, the lips, and/or the appendages. These compositions can be more or less fluid and have the appearance of a cream, a lotion, a milk, a butter, an ointment, a gel, a paste, or a foam. They can also come in solid form like a stick or be applied on the skin in the form of an aerosol. They can be used as a care product and/or as a makeup product for the skin.

These compositions include, in addition, any additive commonly used in the application domain envisioned, as well as the adjuvants necessary for their formulation, such as solvents, thickeners, diluents, antioxidants, colorants, solar filters, self-bronzing principles, pigments, vehicles, preservatives, perfumes, odor absorbents, active cosmetic or pharmaceutical agents, essential oils, vitamins, essential fatty acids, surfactants, film-forming polymers, etc.

In any case, the professional will take care that these adjuvants, as well as their proportions, are chosen in such a way as not to harm the advantageous properties sought in the composition according to the invention. These adjuvants can, for instance, correspond to 0.01 to 20% of the total weight of the composition. When the composition of the invention is an emulsion, the fatty phase may represent 5 to 80% by weight and preferably 5 to 50% by weight relative to the total weight of the composition. The emulsifiers and co-emulsifiers used in the composition will be chosen from among those traditionally used in the domain considered. For example, they may be used in a proportion of 0.3 to 30% by weight relative to the total weight of the composition.

By means of its specific activities, the peptide according to the invention could be used advantageously in a cosmetic composition or for the preparation of a pharmaceutical composition.

In particular, the active principle according to the invention could be used advantageously in a cosmetic composition intended to combat in a preventive and/or curative manner the manifestations of cutaneous aging and, more specifically, to combat and/or to prevent photo-induced aging (photo-aging). Cutaneous manifestations of aging are understood to be any alteration of the external appearance of the skin due to aging, such as, for example, wrinkles and fine wrinkles, shriveled skin, flabby skin, thin skin, lack of elasticity and/or tonus of the skin, dull skin without a glow or pigmentation spots on the skin, as well as any internal alteration of the skin that is not manifested systematically in an altered external appearance, such as, for example, any internal degradation of the skin following an exposure to ultraviolet (UV) rays. The peptide according to the invention, or the composition containing it, will enable combating, in particular, the loss of elasticity and firmness of the skin.

The peptide according to the invention may be used to protect the skin and the appendages against any type of external aggression. The use of the peptide, or of a composition containing it, will allow the skin and the appendages to be protected and to better resist environmental stresses.

The expression "external aggression" is understood to be aggressions which the environment can produce. By way of example, aggressions may be cited such as pollution, UV rays, or even products of an irritating nature such as surfactants, preservatives, and perfumes. Pollution is also understood to be both "outdoor" pollution due, for example, to Diesel-fuel particles, ozone, or heavy metals, as well as "indoor" pollution, which may be due, in particular, to the emissions of the solvents of paint, glue, or wallpaper (such as toluene, styrene, xylene, or benzaldehyde), or even cigarette smoke.

The peptide according to the invention may be advantageously used in a cosmetic composition or for preparing a pharmaceutical composition, as an active photo-protective principle and, more particularly, as a so-called "secondary" active photo-protective principle. Primary active photo-protective principles are, in effect, differentiated from secondary active photo-protective principles. Primary active photo-protective principles are substances that exercise a physical power: they are capable of absorbing UV rays and releasing them in the form of heat in order to protect the skin. Secondary active photo-protective principles are substances that generally have a biological effect; they are, for example, active principles capable of limiting the damage caused to the DNA and to the membranes by UV rays penetrating into the skin.

Thus, the invention also has, as an object, use in a cosmetic composition, or for preparing a pharmaceutical composition, of an effective quantity of peptide as previously described, the peptide, or the composition containing it, being intended to protect the skin from exposure to UV rays or to ionizing radiation during radiotherapy.

The invention also has, as an object, use in a cosmetic composition, or for preparing a pharmaceutical composition, of an effective quantity of peptide according to the invention, the peptide, or the composition containing it, being intended to protect the mitochondria and to increase the synthesis of intracellular ATP in the cells of the skin.

The invention too is related to use in a cosmetic composition, or for preparing a pharmaceutical composition, of an effective quantity of peptide as previously described, the peptide, or the composition containing it, being intended to protect the skin from damage caused by free radicals.

The invention again consists of the use of an active principle according to the invention for preparing a pharmaceutical composition intended to prevent or combat mitochondrial dysfunctions responsible for certain neuromuscular or cardiac degenerations, type II diabetes, or even certain pathologies of aging.

Finally, the invention again consists of a cosmetic-treatment procedure intended to protect the skin and the appendages from external aggressions and to combat cutaneous aging, characterized by the application, onto the skin or the appendages to be treated, of a composition containing an effective quantity of the active principle according to the invention.

Specific embodiments of this cosmetic-treatment procedure also result from the preceding description. Other advantages and characteristics of the invention will be more apparent upon reading the examples given as illustrative and non-restrictive.

EXAMPLE 1

Disclosure of the Stimulating Effect of the SEQ ID No. 1 Peptide on the Synthesis of Intracellular ATP The aim of this study was to determine the effect of the SEQ ID No. 1 peptide on mitochondrial activity. It is the ATP produced by the mitochondria that serves as a biochemical marker for this activity.

Protocol: This study was conducted using an ATP Bioluminescence Assay Kit HS II (Roche Applied Science). Dermal fibroblasts were treated with a 1% solution of a 50-ppm solution containing the SEQ ID No. 1 peptide, representative of the peptide family according to the invention, for a period of 1 to 3 hours. At the end of the incubation time, the tubes were emptied of their medium and rinsed with 2 ml of cold PBS before adding 250 µl of a lysing buffer provided in the kit. The cells of each tube were then scraped up and collected in 14-ml tubes. Each tube was rinsed with 2×500 µl of cold PBS, and the whole was collected again in the respective tubes. Starting with these samples, a dilution to $\frac{1}{12000}$th was achieved in cold PBS before each reading. The ATP measurement was performed on these samples: 50 µl of this dilution was placed in a Luma cuvette and 50 µl of luminol was added. After 10 seconds, the luminescence reading was begun. The values were standardized relative to the quantity of proteins for each sample. The measurements were made using the Biocounter M2010A Luma®/3M equipment.

Results: The ATP measurements show that there was a clear increase in the amount of intracellular ATP after one hour (+43%) and after 3 hours in the cells treated with the SEQ ID No. 1 peptide, compared to the untreated cells.

Conclusion: The SEQ ID No. 1 peptide very significantly stimulates the mitochondrial activity of cutaneous cells as well as fibroblasts.

EXAMPLE 2

Disclosure of the Activator Effect of the SEQ ID No. 2 Peptide on the Enzymatic Activity of Aconitase The aim of this study was to determine the effect of the SEQ ID No. 2 peptide on the enzymatic activity of aconitase. For this, the total enzymatic activity (cytoplasmic and mitochondrial) and the mitochondrial enzymatic activity of aconitase were measured.

Protocol: Normal human fibroblasts were treated with a 1% solution of a 50-ppm SEQ ID No. 2 peptide representative of the peptide family according to the invention, for 48 hr, and were then subjected to UVB radiation of 100 mJ/cm². After irradiation, the cells were treated under the same conditions for another 24 hr. Negative controls were achieved under the same conditions, but in the absence of the SEQ ID No. 2 peptide.

To evaluate the enzymatic activity of aconitase, the fibroblasts were then collected and centrifuged in PBS buffer. A portion of the cells was then processed to measure total enzymatic activity; another portion was used to isolate the mitochondrial fraction according to the following protocol.

The cells were lysed using a Dounce-type homogenizer, and the homogenate was centrifuged cold at 10,000 g for 10 minutes. The pellet, rich in mitochondria, was washed with TES buffer (10 mM Tris, 1 mM EGTA, 0.25 M sucrose) and resuspended in a 0.2-mM trisodium citrate buffer before being used for the enzymatic measurement.

The measurement of the enzymatic activity of aconitase was made using the Oxis Bioxytech Aconitase-340 assay kit (Oxis International), according to the following principle: aconitase causes isomerization of the citrate to isocitrate. The isocitrate is then transformed into α-ketoglutarate by the enzyme isocitrate dehydrogenase. This second reaction is accompanied by the transformation of NADP+ to NADPH. It is the formation of NADPH that is quantified spectrophotometrically at 340 nm. Under the experimental conditions chosen, the rate of NADPH formation is proportional to the quantity of aconitase. The analysis of the kinetics of NADPH appearance enables the concentration of aconitase in the sample to be calculated (in mU/ml)

Results: The results derive from five independent experiments (n=5). The measurements of total enzymatic activity for aconitase (FIG. 1) show an increase of 56.3% in the activity of cells treated with the SEQ ID No. 2 peptide compared with untreated control cells. When the cells were irradiated with UVB rays, on the other hand, a reduction of 33% was observed in this activity. The treatment before and after UVB irradiation with the peptide with SEQ ID No. 5 enabled the observed reduction to be limited in untreated control cells.

The measurements of the enzymatic activity of mitochondrial aconitase (FIG. 2) show comparable results.

Figure 1:
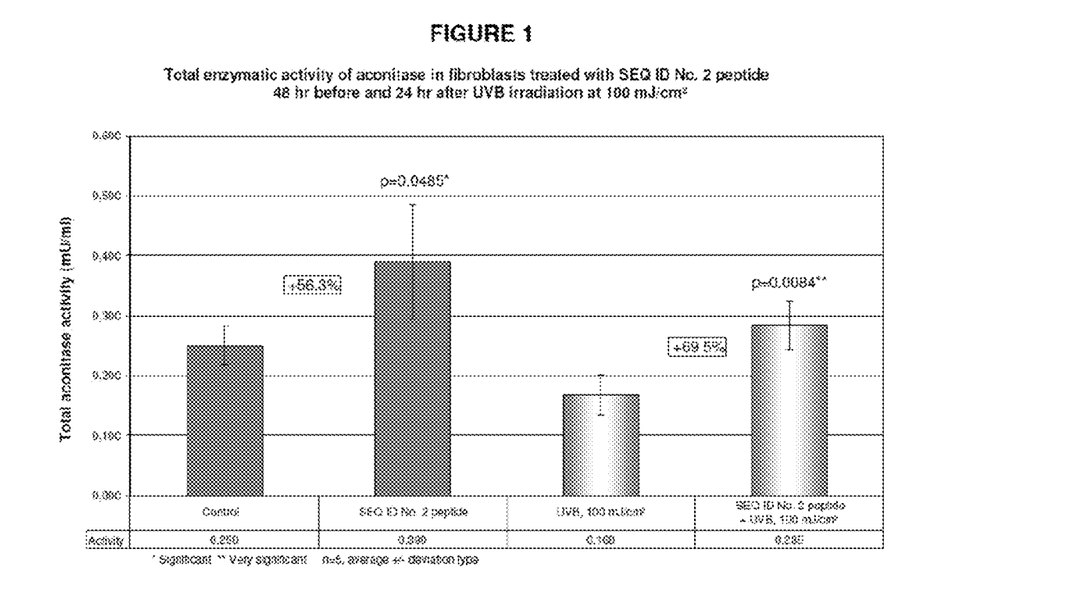
FIG. 1 represents the results of measuring the total enzymatic activity of aconitase in fibroblasts treated with SEQ ID No. 2 peptide and irradiated or not with UVB rays.
Figure 2:
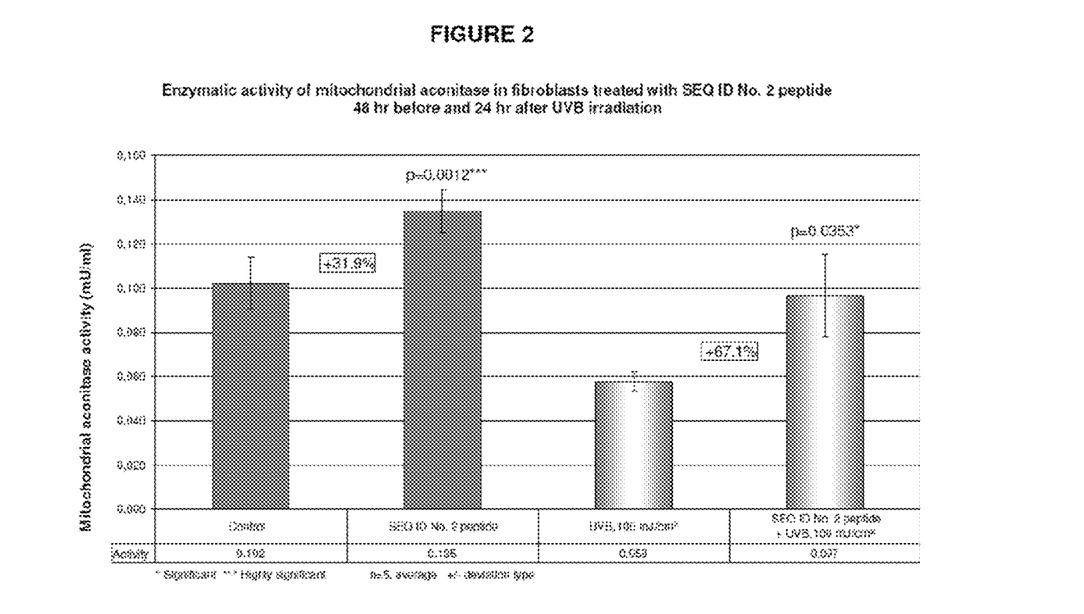
FIG. 2 represents the results of measuring specific enzymatic activity of mitochondrial aconitase in fibroblasts treated with SEQ ID No. 2 peptide and irradiated or not with UVB rays.

The results are presented in FIGS. 1 and 2.

Conclusions: The SEQ ID No. 2 peptide, in a concentration of 0.05 ppm, strongly stimulates the enzymatic activity of the cytoplasmic and mitochondrial aconitase in cutaneous cells. The action of the SEQ ID No. 2 peptide protects the cells and mitochondria from a UVB stressor.

EXAMPLE 3

Evaluation of the Protective Effect of the SEQ ID No. 2 Peptide on Cutaneous Cells Subjected to Ultraviolet (UVB) Rays The aim of this study was to determine the protective effect of the SEQ ID No. 2 peptide on dermal fibroblasts subjected to stress from UVB rays. For this, cellular viability tests were performed using the MTT technique.

Protocol: Human dermal fibroblasts were treated with a 1% solution of a 50-ppm solution of SEQ ID No. 2 peptide for 24 hr, irradiated with UVB rays (25-100 mJ/cm²), and then cultivated for another 24 hr in the presence of the same concentration of SEQ ID No. 2 peptide. Untreated and non-irradiated controls, as well as untreated but irradiated controls were achieved under the same conditions. At the end of the experiment, the cells were incubated in a solution containing 0.1 mg/ml of MTT (3-[4,5-dimethylthiazolyl]-2,5-diphenyl-2H-tetrazolium bromide). This compound is absorbed by living cells and then metabolized by the mitochondrial enzymes into a blue-violet compound, formazan, which is measured spectrophotometrically at 540 nm. The Absorbance (OD) is then directly proportional to the mitochondrial enzymatic activity as well as to the number of living cells.

Results:

| Conditions | Control without peptide | Peptide | Control, UVB | Peptide + UVB | Control, UVB | Peptide + UVB | Control, UVB | Peptide + UVB |
|---|---|---|---|---|---|---|---|---|
| SEQ ID No. 2 peptide (ppm) | — | 0.5 | — | 0.5 | — | 0.5 | — | 0.5 |

-continued

| Conditions | Control without peptide | Peptide | Control, UVB | Peptide + UVB | Control, UVB | Peptide + UVB | Control, UVB | Peptide + UVB |
|---|---|---|---|---|---|---|---|---|
| UVB irradiation (mJ/cm$^2$) | — | — | 25 | 25 | 50 | 50 | 100 | 100 |
| % viability | 100 | 114.24 | 94.76 | 108.24 | 88.59 | 102.09 | 76.43 | 98.18 |

Evaluation of cellular viability by the MTT technique showed, on the one hand, that the SEQ ID No. 2 peptide increases cellular viability, independent of any UVB radiation, and on the other hand, that UVB irradiation had a quantity-dependent cytotoxic effect on the human fibroblasts, but that this cytotoxic effect was not exhibited in the presence of 0.5 ppm of SEQ ID No. 2 peptide.

Conclusions: The SEQ ID No. 2 peptide, in a concentration of 0.5 ppm, increases cellular viability and, on the other hand, effectively protects cutaneous cells against the cytotoxic effects of UVB rays.

EXAMPLE 4

Evaluation of the Protective Effect of the SEQ ID No. 2 Peptide on Cutaneous Cells Subjected to Oxidative Stress The aim of this study was to determine the protective effect of the SEQ ID No. 2 peptide with respect to dermal fibroblasts subjected to an oxidative stress caused by oxygenated water ($H_2O_2$) in a concentration of 4 mM or 5 mM. For this, cellular viability tests were performed using the MTT technique.

Protocol: Human dermal fibroblasts were treated with a 1% solution of a 50-ppm SEQ ID No. 2 peptide for 24 hours, subjected to an oxidative stress caused by 4 mM or 5 mM of $H_2O_2$ for 30 minutes, and then cultivated for another 24 hours in the presence of the same concentration of SEQ ID No. 2 peptide. Controls treated with neither the peptide nor $H_2O_2$ and controls treated with the peptide alone were achieved under the same conditions. At the end of the experiment, the cells were incubated in a solution containing 0.1 mg/ml of MTT (3-[4,5-dimethylthiazole-2-yl]-2,5-diphenyltetrazolium bromide) according to the protocol described in example 3

Results:

| Conditions | Control without peptide | Peptide | Control, $H_2O_2$ | Peptide + $H_2O_2$ | Control, $H_2O_2$ | Peptide + |
|---|---|---|---|---|---|---|
| SEQ ID No. 2 peptide (ppm) | — | 0.5 | — | 0.5 | — | 0.5 |
| $H_2O_2$-, 30 min | — | — | 4 mM | 4 mM | 5 mM | 5 mM |
| % viability | 100 | 121.13 | 91.71 | 102.04 | 68.92 | 94.40 |

The evaluation of cellular viability by the MTT technique showed, on the one hand, that the SEQ ID No. 2 peptide increases cellular viability, independent of an oxidative stress, and on the other hand, that an oxidative stress caused by 4 mM or 5 mM of $H_2O_2$ for 30 min had a quantity-dependent cytotoxic effect on the human fibroblasts, but that this cytotoxic effect was not exhibited in the presence of 0.5 ppm of SEQ ID No. 2 peptide.

Conclusions: The SEQ ID No. 2 peptide, in a concentration of 0.5 ppm, increases cellular viability and effectively protects cutaneous cells against the cytotoxic effects of an oxidative stress.

EXAMPLE 5

Evaluation of the Cytoprotective Effect of the SEQ ID No. 2 Peptide on Cutaneous Cells Subjected to Ultraviolet (UVB) Rays A study of the cytoprotective effect of SEQ ID No. 2 peptide was made by evaluating the damage caused at the DNA level. This study was done using the comet (or single-cell gel electrophoresis) test, a quick and sensitive microelectrophoretic technique that enables breaks in the DNA to be visualized and quantified in individual cells.

Protocol: Primary human fibroblasts were seeded in 100-diameter dishes. When the cells reached 70% coalescence, they were treated with SEQ ID No. 2 peptide diluted to 1% (starting from a 50-ppm solution) for 24 hours. The cells were then subjected to UVB irradiation at 100 mJ/cm$^2$, then cultivated in the presence of the peptide for another 24 hours. The dishes not treated with the peptide served as controls. A cellular suspension of 100,000 cells/ml was then achieved, 500 µl were removed, inserted into an agarose solution, and run between slide and cover glass. The cells were lysed in the cold. The DNA was then denatured with an alkaline buffer and subjected to a brief electrophoresis (250 mA for 30 minutes), and stained with propidium iodate. The slides were then observed under a fluorescence microscope. An altered cell sees its DNA stretch toward the anode in proportion to the number of breaks present in the DNA, and it forms a "comet". The highly degraded DNA is found in the "tail" of the comet. An intact cell remains round, and its DNA is then packed into the area of the comet "head".

The evaluation of DNA breaks was done using image-analyzer software that enables the percentage of DNA degradation to be determined, by means of a quantitative evaluation of the "tail moment", a parameter defined as the product of the length of the comet by the percentage of DNA in its distal portion.

Results: The table below represents the evaluation of the "tail moments" measured in fibroblasts irradiated with UVB and treated or not with the SEQ ID No. 2 peptide.

| Study conditions | Measurement of "tail moment" | % of "tail moment" relative to UV control |
|---|---|---|
| Control, UVB | 106,563 | 100 |
| UVB + SEQ ID No. 2 peptide | 80,221 | 75 |

The results obtained show that the cells subjected to UVB irradiation, in the absence of the SEQ ID No. 2 peptide (UVB control) exhibit the largest "tail moment", that is, the condition in which the DNA is most damaged. On the other hand, the cells treated with 0.5-ppm peptide with SEQ ID No. 2 have a "tail moment", that is DNA damage, reduced by 25%.

Conclusion: The SEQ ID No. 2 peptide plays an important role in protecting the DNA of cutaneous cells subjected to UVB irradiation.

EXAMPLE 6

Evaluation of the Action of the SEQ ID No. 2 Peptide on the Ultra-Structure of Mitochondria The aim of this study was to determine the action of the SEQ ID No. 2 peptide on mitochondria, by observing the ultrastructures with the electron microscope.

Protocol: Normal human keratinocytes were treated with a 1% solution of a 50-ppm mother-solution of SEQ ID No. 2 peptide for 72 hours. Negative controls were achieved under the same conditions, but in the absence of the said peptide.

The cells were then fixed using Karnovsky's fixative (20 ml of 16% paraformaldehyde/8 ml of 50% glutaraldehyde/25 ml of 0.2 M sodium phosphate buffer/25 ml of water) for 1 hr at ambient temperature, and then left overnight at 4° C. The culture media were scraped into the Karnovsky's fixative and then the cells were centrifuged for 5 minutes at 5000 rpm. The supernatant was isolated and the pellet resuspended in 1 ml of 0.1 M cacodylate. The samples were then kept at 4° C. until their processing for electron microscopy observation.

Results: The organelles of the cells treated with SEQ ID No. 2 peptide exhibited ultrastructural characteristics suggesting an increase in metabolic activity. In particular, the characteristics of the mitochondrial population and the abundance of elements of the Golgi apparatus are in agreement with a stimulation of metabolic synthesis.

Conclusion: The SEQ ID No. 2 peptide has a stimulating action on mitochondrial activity.

EXAMPLE 7

Preparation of Compositions

1. Sunscreen Cream

| Trade name | International Nomenclature of Cosmetic Ingredients (INCI) names | % w/w |
|---|---|---|
| PHASE A | | |
| Demineralized water | Aqua (water) | In sufficient quantity |
| Pemulen ® TR-1 | Acrylates/C10-30 alkyl acrylate cross-polymer | 0.40 |
| Glycerine | Glycerin | 3.00 |
| Nipastat ® Sodium | Sodium methylparaben (and) sodium ethylparaben (and) sodium butylparaben (and) sodium propylparaben (and) sodium isobutylparaben | 0.15 |
| PHASE B | | |
| Parsol ® MCX | Ethylhexyl methoxycinnamate | 7.50 |
| Eusolex ® 4360 | Benzophenone-3 | 3.00 |
| Parsol ® 1789 | Butyl methoxydibenzoyl-methane | 2.00 |
| Myritol ® 318 | Caprylic/capric triglyceride | 4.00 |
| Emulgade ® SEV | Hydrogenated palm glycerides (and) ceteareth-20 (and) ceteareth-12 (and) cetearyl alcohol | 5.00 |
| Propylparaben | Propylparaben | 0.15 |
| Nacol ® 16-98 | Cetyl alcohol | 1.00 |
| PHASE C | | |
| TEA | Triethanolamine | 0.20 |
| PHASE D | | |
| SEQ ID No. 2 peptide | | 3 ppm |
| Perfume | Perfume (fragrance) | In sufficient quantity |
| Colorant | | In sufficient quantity |

The constituents of phase A and of phase B are heated separately to a temperature between 70° C. and 75° C. Phase B is emulsified in phase A while stirring. Phase C is added, at 45° C., while increasing the stirring. Phase D is then added when the temperature was below 40° C. Cooling is continued to 25° C. with brisk stirring.

2. After-Sun Milk

| Trade name | INCI names | % w/w |
|---|---|---|
| PHASE A | | |
| Montanov ™ L | C14-22 alcohols (and) C12-20 alkyl glucoside | 3.00 |
| Waglinol 2559 | Cetearyl isononanoate | 4.00 |
| Tegosoft ® TN | C12-15 alkyl benzoate | 3.00 |
| Apricot kernel oil | *Prunus armeniaca* (apricot) kernel oil | 2.00 |
| Avocado oil | *Persea gratissima* (avocado) oil | 1.00 |
| Abil ® 350 | Dimethicone | 1.00 |
| PHASE B | | |
| Demineralized water | Aqua (water) | In sufficient quantity |
| PHASE C | | |
| Simulgel ™ EG | Sodium acrylate/acryloyl-dimethyl taurate copolymer (and) isohexadecane (and) polysorbate 80 copolymer (and) polysorbate 80 | 0.4 |
| PHASE D | | |
| Phenonip ® | Phenoxyethanol (and) methylparaben (and) ethylparaben (and) butylparaben (and) propylparaben (and) isobutylparaben ethylparaben and propylparaben and butylparaben | 0.30 |
| Germall ® 115 | Imidazolidinyl urea | 0.20 |
| PHASE E | | |
| SEQ ID No. 2 peptide | | 0.1 ppm |

Prepare phase A while stirring. Incorporate the xanthan gum gradually, with dispersant stirring. Phases C and D will be incorporated once the gel has set. Phase E, prepared in advance to the point of perfect DHA dissolution, will then be added. Adjust the pH, if necessary, to 4-4.5. Color and perfume.

3. Anti-Aging Cream

| Trade name | INCI names | % w/w |
|---|---|---|
| PHASE A | | |
| Montanov ™ 68 | Cetearyl alcohol (and) cetearyl glucoside | 6.00 |
| Squalane | Squalane | 3.00 |
| Cetiol ® SB 45 | *Butyrospermum parkii* (Shea butter) | 2.00 |
| Waglinol 250 | Cetearyl ethylhexanoate | 3.00 |
| Amerchol L-101 | Mineral oil (and) lanolin alcohol | 2.00 |
| Abil ® 350 | Dimethicone | 1.50 |
| BHT | Butylhydroxytoluene | 0.01 |
| Coenzyme Q10 | Ubiquinone | 0.10 |
| PHASE B | | |
| Avocado oil | *Persea gratissima* (avocado) oil | 1.25 |
| Phenonip ® | Phenoxyethanol (and) methylparaben (and)\ ethylparaben (and) butylparaben (and) propylparaben (and) isobutylparaben | 0.75 |
| PHASE C | | |
| Demineralized water | Aqua (water) | In sufficient quantity |
| Butylene glycol | Butylene glycol | 2.00 |
| Glucam ™ E10 | Methyl gluceth-10 | 1.00 |
| Allantoin | Allantoin | 0.15 |
| Carbopol ® Ultrez 10 | Carbomer | 0.20 |
| PHASE D | | |
| TEA | Triethanolamine | 0.18 |
| PHASE E | | |
| SEQ ID No. 1 peptide | | 0.5 ppm |
| GP4G ® | Water (and) *Artemia* extract | 1.50 |
| Collaxyl ® | Water (and) butylene glycol (and) hexapeptide-9 | 3.00 |
| PHASE F | | |
| Perfume | Perfume (fragrance) | In sufficient quantity |
| Colorant | | In sufficient quantity |

Prepare and melt phase A at 65-75° C. Heat phase C to 65-70° C. Phase B is added to phase A just before emulsifying A in B. At about 45° C., the carbomer is neutralized by the addition of phase D. Phase E is then added with light stirring, and cooling is continued to 25° C. Phase F is then added, if desired.

4. Daytime Protection Cream

| Trade name | INCI names | % w/w |
|---|---|---|
| PHASE A | | |
| Emulium delta ® | Cetyl alcohol (and) glyceryl stearate (and) PEG-75 stearate (and) ceteth-20 (and) steareth-20 | 4.00 |
| Lanette O | Cetearyl alcohol | 1.50 |
| DC 200 Fluid ®/100 cs | Dimethicone | 1.00 |
| DUB 810C | Coco caprylate/caprate | 1.00 |
| DPPG | Propylene glycol dipelargonate | 3.00 |
| DUB DPHCC | Dipentaerythrityl hexacaprylate/hexacaprate | 1.50 |
| Cegesoft ® PS 6 | Vegetable oil | 1.00 |
| Vitamin E | Tocopherol | 0.30 |
| Phenonip ® | Phenoxyethanol (and) methylparaben (and) ethylparaben (and) butylparaben (and) propylparaben (and) isobutylparaben | 0.70 |
| PHASE B | | |
| Demineralized water | Aqua | In sufficient quantity, 100 |
| Glycerine | Glycerin | 2.00 |
| Carbopol ® ETD 2020 | Acrylates/C10-30 alkyl acrylate cross-polymer | 0.15 |
| Keltrol CG-BT | Xanthan gum | 0.30 |
| PHASE C | | |
| Sodium hydroxide (10% solution) | Sodium hydroxide | 0.30 |
| PHASE D | | |
| Demineralized water | Aqua | 5.00 |
| Stay-C ® 50 | Sodium ascorbyl phosphate | 0.50 |
| PHASE E | | |
| Butylene glycol | Butylene glycol | 2.00 |
| Dekaben CP | Chlorphenesin | 0.20 |
| PHASE F | | |
| GP4G ® | Water (and) *Artemia* extract | 1.00 |
| SEQ ID No. 2 peptide | | 5 ppm |

Prepare phase A and heat to 75° C. while stirring. Prepare phase B, while dispersing the Carbopol®, and then the xanthan gum while stirring. Let rest. Heat to 75° C. At temperature, emulsify A in B with rotor-stator stirring. Neutralize with phase C while stirring rapidly. After cooling to 40° C., add phase D and then phase E. Cooling is continued with light stirring, and phase F is added.

The invention claimed is:

1. A cosmetic or pharmaceutical composition, comprising: a peptide in a physiologically acceptable medium, said peptide being an active-principle protector of mitochondria, alone or in association with at least one other active principle, wherein, said peptide is capable of activating aconitase, said peptide includes 3 to 6 amino acid residues, and said peptide has a sequence according to formula (I):

$$R_1\text{-}(AA)_n\text{-}X_1\text{-}X_2\text{-}X_3\text{-}X_4\text{-}X_5\text{-}X_6\text{-}(AA)_p\text{-}R_2$$

in which $X_1$ is serine, $X_2$ is cysteine, $X_3$ is threonine or isoleucine, $X_4$ is glutamine, asparagine, or no amino acid, $X_5$ is threonine, serine, or no amino acid, $X_6$ is isoleucine, glutamine, or no amino acid, AA represents any amino acid, or derivative thereof, lacking sequence of aconitase, and n and p are 0

$R_1$ represents the primary amine function of the N-terminal amino acid, free or substituted with a protector group selected from the group consisting of an acetyl group, a benzoyl group, a tosyl group, and a benzyloxycarbonyl group, $R_2$ represents the hydroxyl group of the carboxylic acid function of the C-terminal amino acid, free or substituted with a protector group selected from (i) an alkyl chain of $C_1$ to $C_{20}$ or (ii) an $NH_2$ group, an NHY group, or an NYY group, with Y representing a alkyl chain of $C_1$ to $C_4$.

2. The composition according to claim 1, wherein said peptide has a sequence selected from the group consisting of:

| | |
|---|---|
| (SEQ ID No. 1) | Ser-Cys-Ile-Asn-Thr; |
| (SEQ ID No. 2) | Ser-Cys-Ile-Asn-Thr-NH$_2$; |
| (SEQ ID No. 3) | Ser-Cys-Thr-Asn-Thr; |
| (SEQ ID No. 4) | Ser-Cys-Thr-Asn-Thr-NH$_2$; |
| (SEQ ID No. 5) | Ser-Cys-Ile-Asn-Ser; |
| (SEQ ID No. 6) | Ser-Cys-Ile-Gln; and |
| (SEQ ID No. 7) | Ser-Cys-Thr. |

3. The composition according to claim 2, wherein said peptide has the sequence SEQ ID No. 1.

4. The composition according to claim 2, wherein said peptide has the sequence SEQ ID No. 2.

5. The composition according to claim 1, wherein said peptide possesses at least one functional group protected by a protector group, and said protector group is at least one of (i) an acylation or an acetylation of the amino-terminal end and (ii) an amidation or an esterification of the carboxy-terminal end.

6. The composition according to claim 1, wherein said peptide is present in the composition in a concentration between approximately 0.0005 and 500 ppm.

7. The composition according to claim 6, wherein said peptide is present in a concentration between 0.01 and 5 ppm.

8. The composition according to claim 1, wherein said peptide is solubilized in advance in one or several cosmetically or pharmaceutically acceptable solvents selected from the group consisting of water, glycerol, ethanol, propylene glycol, butylene glycol, dipropylene glycol, ethoxylated or propoxylated diglycols, cyclic polyols, petroleum jelly, a vegetable oil, and mixture thereof.

9. The composition according to claim 1, wherein the physiological medium is a cosmetically or dermatologically acceptable medium for topical application.

10. The composition according to claim 1, further comprising at least one other active principle promoting the action of the said peptide.

11. The composition according to claim 10, wherein the other active principle is selected from the group consisting of active antioxidant principles, active principles stimulating the synthesis of the extracellular matrix, active principles stimulating cellular energy metabolism, and combinations thereof.

12. A method for protecting the mitochondria and for increasing the synthesis of intracellular ATP in the cells of the skin, comprising administering a cosmetic composition according to claim 1 having an effective amount of active principle to a subject in need thereof.

13. The method according to claim 12, wherein the composition protects the skin and the appendages against external aggression.

14. The method according to claim 13, wherein the external aggression is from UV rays.

15. The method according to claim 12, wherein the composition protects from or treats the damage caused to the skin and to the appendages by free radicals.

16. The method according to claim 12, wherein the composition protects from or treats the cutaneous signs of aging and/or of photo-aging.

17. A method of preparing a pharmaceutical composition intended to protects from or to combat mitochondrial dysfunctions responsible for at least one of certain neuromuscular or cardiac degeneration, type II diabetes, and certain pathologies of aging, comprising adding to a physiologically acceptable medium, a peptide being an active-principle protector of mitochondria, alone or in association with at least one other active principle, wherein, said peptide is capable of activating aconitase, said peptide includes 3 to 6 amino acid residues, and said peptide has a sequence according to formula (I):

$$R_1\text{-}(AA)_n\text{-}X_1\text{-}X_2\text{-}X_3\text{-}X_4\text{-}X_5\text{-}X_6\text{-}(AA)_p\text{-}R_2$$

in which $X_1$ is serine, $X_2$ is cysteine, $X_3$ is threonine or isoleucine, $X_4$ is glutamine, asparagine, or no amino acid, $X_5$ is threonine, serine, or no amino acid, $X_6$ is isoleucine, glutamine, or no amino acid, AA represents any amino acid, or derivative thereof, lacking sequence of aconitase, and n and p are 0, $R_1$ represents the primary amine function of the N-terminal amino acid, free or substituted with a protector group selected from the group consisting of an acetyl group, a benzoyl group, a tosyl group, and a benzyloxycarbonyl group, $R_2$ represents the hydroxyl group of the carboxylic acid function of the C-terminal amino acid, free or substituted with a protector group selected from (i) an alkyl chain of $C_1$ to $C_{20}$ or (ii) an $NH_2$ group, an NHY group or an NYY group, with Y representing a alkyl chain of $C_1$ to $C_4$.

18. A method of protecting skin and appendages from external aggressions, comprising topically applying to the skin or the skin appendages of a subject in need thereof, a cosmetic composition according to claim 1 having an effective amount of active principle.

* * * * *

SEQUENCE LISTING

<160> NUMBER OF SEQ ID NOS: 7

<210> SEQ ID NO 1
<211> LENGTH: 5
<212> TYPE: PRT
<213> ORGANISM: Artificial
<220> FEATURE:
<223> OTHER INFORMATION: Synthetic Peptide

<400> SEQUENCE: 1

Ser Cys Ile Asn Thr
1               5

<210> SEQ ID NO 2
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 2

Ser Cys Ile Asn Thr
1               5

<210> SEQ ID NO 3
<211> LENGTH: 5
<212> TYPE: PRT
<213> ORGANISM: Artificial
<220> FEATURE:
<223> OTHER INFORMATION: Synthetic Peptide

<400> SEQUENCE: 3

Ser Cys Thr Asn Thr
1               5

<210> SEQ ID NO 4
<211> LENGTH: 5
<212> TYPE: PRT
<213> ORGANISM: Artificial
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 4

Ser Cys Thr Asn Thr
1               5

<210> SEQ ID NO 5
<211> LENGTH: 5
<212> TYPE: PRT
<213> ORGANISM: Artificial
<220> FEATURE:
<223> OTHER INFORMATION: Synthetic Peptide

<400> SEQUENCE: 5

Ser Cys Ile Asn Ser
1               5

<210> SEQ ID NO 6
<211> LENGTH: 4

```
<212> TYPE: PRT
<213> ORGANISM: Artificial
<220> FEATURE:
<223> OTHER INFORMATION: Synthetic Peptide

<400> SEQUENCE: 6

Ser Cys Ile Gln
1

<210> SEQ ID NO 7
<211> LENGTH: 3
<212> TYPE: PRT
<213> ORGANISM: Artificial
<220> FEATURE:
<223> OTHER INFORMATION: Synthetic Peptide

<400> SEQUENCE: 7

Ser Cys Thr
1
```